US006858219B2

(12) United States Patent
Evans et al.

(10) Patent No.: US 6,858,219 B2
(45) Date of Patent: Feb. 22, 2005

(54) METHODS FOR STERILIZING MALE MAMMALS

(75) Inventors: Scott Evans, Santa Ana, CA (US); Richard J. Greff, St. Pete Beach, FL (US); James I. Wright, Villa Park, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 10/394,231

(22) Filed: Mar. 24, 2003

(65) Prior Publication Data

US 2003/0185758 A1 Oct. 2, 2003

Related U.S. Application Data

(63) Continuation of application No. 10/223,438, filed on Aug. 20, 2002, which is a continuation of application No. 09/848,312, filed on May 4, 2001, now abandoned, which is a continuation of application No. 08/802,252, filed on Feb. 19, 1997, now abandoned, which is a continuation of application No. 08/655,822, filed on May 31, 1996, now abandoned.

(51) Int. Cl.$^7$ .......................... A61K 9/08; A61K 17/30; A61P 13/16
(52) U.S. Cl. ....................... 424/422; 424/423; 424/430
(58) Field of Search .............................. 424/422, 423, 424/430, 486–88

(56) References Cited

U.S. PATENT DOCUMENTS

| | | | |
|---|---|---|---|
| 4,079,124 A | | 3/1978 | Winchell |
| 4,631,188 A | | 12/1986 | Stoy et al. |
| 4,795,741 A | | 1/1989 | Lischiner et al. |
| 4,847,065 A | | 7/1989 | Akimova et al. |
| 4,938,763 A | | 7/1990 | Dunn et al. |
| 4,938,961 A | | 7/1990 | Dunn et al. |
| 4,999,188 A | | 3/1991 | Solodovnik et al. |
| 5,202,352 A | | 4/1993 | Okada et al. |
| 5,443,454 A | | 8/1995 | Tanabe et al. |
| 5,525,334 A | | 6/1996 | Ito et al. |
| 5,580,568 A | | 12/1996 | Evans et al. |
| 5,667,767 A | | 9/1997 | Evans et al. |
| 5,695,480 A | | 12/1997 | Evans et al. |
| 5,702,361 A | | 12/1997 | Evans et al. |
| 6,103,254 A | * | 8/2000 | Wallace et al. |

FOREIGN PATENT DOCUMENTS

| | | |
|---|---|---|
| JP | 3-252799 | 9/1991 |
| JP | 4-55273 | 3/1992 |
| JP | 4-301502 | 9/1992 |
| JP | 406107549 | 4/1994 |
| WO | 85/00969 | 3/1985 |
| WO | 97/04656 | 2/1997 |
| WO | 97/04657 | 2/1997 |
| WO | 97/04813 | 2/1997 |

OTHER PUBLICATIONS

Amdur, et al. "Toxic Effects of Metals." *Toxicology.* 4$^{th}$ ed. pp. 661–664.

Chaloupka, et al. "Technical Feasibility and Histopathologic studies of Ethylene Vinyl Copolymer (EVAL) Using a Swine Endovascular Embolization Model." *Am J. Neuroradiology.* 15(6): 1107–1115 (1994).

Guglielmi, et al. "Electrothrombosis of Saccular Aneurysms via Endovascular Approach." *J. Neurosurg.* 75: 8–14 (1991).

Kinugasa, et al. "Early Treatment of Subarchnoid Hemorrhage After Preventing Rerupture of an Aneurysm." *J. Neurosurg.* 83: 34–41 (1995).

Kinugasa, et al. "Prophylactic Thrombosis to Prevent New Bleeding and to Delay Aneurysm Surgery." *Neurosurg.* 36(4): 661–667 (1995).

Kinugasa, et al. "Direct Thrombosis of a Pseudoaneurysm after Obliteration of a Carotid–Cavernouse Fistula with Cellulose Acetate Polymer: Technical Case Report." *Neurosurg.* 35(4): 755–760 (1994).

Kinugasa, et al. "Direct Thrombosis of Aneurysms with Cellulose Acetate Polymer, Part II: Preliminary Clinical Experience." *J. Neurosurg.* 77: 501–507 (1992).

Link, et al. "Hydrogel Embolic Agents Theory and Practice of Adding Radio–Opacity." *Invest. Radiol.* 29(8): 746–751 (1994).

Mandai, et al. "Direct Thrombosis of Aneurysms with Cellulose Acetate Polymer: Part I: Results on Thrombosis in Experimental Aneurysms." *J. Neurosurg.* 77: 497–500 (1992).

Miyatake, et al. "Cobb's Syndrome and its Treatment with Embolization." *J. Neurosurg.* 72: 497–499 (1990).

Naitoh, et al. "Removal of Beta–2–Microglubulin by Diffusion Alone is Feasible Using Highly Permeable Dialysis Membranes." *Trans. Am. Soc. Artif. Inter. Organs.* XXXIV: 630–634 (1988).

Park, et al. "New Polymers for Therapeutic Embolization." Poster #47, Meeting of the Radiological Society of North America. (1993).

Sadato, et al. "Experimental Study and Clinical Use of Poly(vinyl acetate) Emulsions as Liquid Embolisation Material." *Neuroradiology.* 36: 634–641 (1994).

Su, et al. "Histopathological Studies of a New Liquid Embolization Method Using Estrogen–Alcohol and Polyvinyl Acetate." *Surg. Heurol,* 36(1): 4–11 (1991).

(List continued on next page.)

*Primary Examiner*—Edward J Webman
(74) *Attorney, Agent, or Firm*—Foley & Lardner LLP

(57) ABSTRACT

Disclosed are compositions suitable for use in embolizing blood vessels which compositions comprise a polymer, a biocompatible solvent and a contrast agent. The polymer is selected from the group consisting of polyacrylonitrile, polyurethane, polyvinylacetate, cellulose acetate butyrate, nitrocellulose and copolymers of urethane/carbonate and copolymers of styrene/maleic acid.

16 Claims, No Drawings

OTHER PUBLICATIONS

Sugiu, et al. Direct Thrommbosis of Experimental Aneurysms with Cellulose Acetate Polymer (CAP): Technical Aspects, Angiographic Follow Up, and Histological Study *J. Neurosurg.* 83: 531–538 (1995).

Taki, et al. "A New Liquid Material for Embolization of Artiovenous Malformations." *AJNR.* 11: 163–168 (1990).

Taki, et al. "Selection and Combination of Various Endovascular Techniques in the Treatment of Giant Aneurysms." *J. Neurosurg.* 77: 37–42 (1992).

Taki, et al. "Possibility and Limit of Intravascular Surgery." *Medical Tribune.* 46–47 (1989).

Terada, et al. "Embolization of Arteriovenous Malformations with Peripheral Aneurysms using Ethylene Vinyl Alcohol Copolymer." *J. Neurosurg.* 75: 655–660 (1991).

Yamashita, et al. "Characteristics of Ethylene Vinyl Alcohol Copolymer (EVAL) Mixtures." *AJNR.* 15: 1103–1105 (1994).

* cited by examiner

METHODS FOR STERILIZING MALE MAMMALS

CROSS-REFERENCE TO RELATED APPLICATIONS

This application is a continuation of U.S. application Ser. No. 10/223,438, filed Aug. 20, 2002, which is a continuation of U.S. application Ser. No. 09/848,312, filed May 4, 2001, now abandoned, which is a continuation of U.S. application Ser. No. 08/802,252, filed Feb. 19, 1997, now abandoned, which is a continuation of Ser. No. 08/655,822, filed May 31, 1996, now abandoned, which application is incorporated herein by reference in its entirety.

BACKGROUND OF THE INVENTION

1. Field of the Invention

This invention is directed to novel compositions suitable for use in embolizing blood vessels. In particular, this invention is directed to embolizing compositions comprising a biocompatible polymer, a biocompatible solvent and a contrasting agent. The compositions of this invention find particular utility in embolizing blood vessels in, for example, the treatment of aneurysms and in ablating diseased tissues.

This invention is also directed to methods for sterilizing male mammals generally and male humans in particular. In these methods, a composition comprising a biocompatible polymer and a biocompatible solvent is delivered to the vas deferens of the male mammal.

The biocompatible polymer is selected to be soluble in the biocompatible solvent, but insoluble in the aqueous fluid of the vas deferens. The biocompatible solvent is miscible or soluble in this aqueous fluid and, upon contact with this fluid, the biocompatible solvent quickly diffuses away whereupon the biocompatible polymer precipitates to form an occlusion in the vas deferens which blocks the passage of spermatic fluid.

A significant advantage of the methods of this invention is that the sterilization can be reversed merely by dissolving the biocompatible polymer forming the occlusion with the biocompatible solvent.

References

1 Mandai, et al., "Direct Thrombosis of Aneurysms with Cellulose Acetate Polymer", J. Neurosurg., 22:497–500 (1992)
2 Kinugasa, et al., "Direct Thrombosis of Aneurysms with Cellulose Acetate Polymer", J. Neurosurg., 22:501–507 (1992)
3 Greff, et al., U. S. patent application Ser. No. 08/508,248, for "Cellulose Diacetate Compositions for Use in Embolizing Blood Vessels, filed Jul. 27, 1995.
4 Greff, et al., U.S. patent application Ser. No. 08/507,863, for "Novel Compositions for Use in Embolizing Blood Vessels", filed Jul. 27, 1995.
5 Evans, et al., U.S. patent application Ser. No. 08/655,987 for "Methods for the Reversible Sterilization of Male Mammals, filed concurrently herewith as Attorney Docket No. 018413-007
6 Evans, et al., U.S. patent application Ser. No. 08/656,394 for "Methods for the Reversible Sterilization of Female Mammals, filed concurrently herewith as Attorney Docket No. 018413-014
7 Goldsmith, et al., "Transcutaneous Procedures for Male Sterilization," Adv. Contracept., 1:355–361 (1985).
8 Chvapil, et al., "Occlusion of the Vas Deferens in Dogs with a Biocompatible Hydrogel Solution," J. Reproductive Med., 35(9):905–910 (1990).
9 Zhao Sheng-cai, "Vas Deferens Occlusion by Percutaneous Injection of Polyurethane Elastomer Plugs: Clinical Experience and Reversibility," Contraception, 41:453–459 (1990).
10 Sethi, et al., "Histological Changes in the Vas Deferens of Rats After Injection of a New Male Antifertility Agent 'SMA' and Its Reversibility," Contraception, 41:333–339 (1990).
11 Guha, et at., "Time-Controlled Injectable Occlusion of the Vas Deferens," contraception, 41:323–331(1990).
12 Sethi, et al., "Safety Evaluation of a Male Injectable Antifertility Agent, Styrene Maleic Anhydride, in Rats," Contraception, 2:217–227 (1989).
13 Kinugasa, et al., "Direct Thrombosis of Aneurysms with Cellulose Acetate Polymer", J. Neurosurg., 77:501–507 (1992).
14 Kinugasa, et al., "Early Treatment of Subarachnoid Hemorrhage After Preventing Rerupture of an Aneurysm", J. Neurosurg., 34–41 (1995).
15 Kinugasa, et al., "Prophylactic Thrombosis to Prevent New Bleeding and to Delay Aneurysm Surgery", Neurosurg., 661 (1995).
16 Taki, et al., "Selection and Combination of Various Endovascular Techniques in the Treatment of Giant Aneurysms", J. Neurosurg., 22:37–42 (1992).
17 Rabinowitz, et al., U.S. Pat. No. 3,527,224, for "Method of Surgically Bonding Tissue Together", issued Sep. 8, 1970.
18 Hawkins, et al., U.S. Pat. No. 3,591,676, for "Surgical Adhesive Compositions", issued Jul. 6, 1971.
19 Stoy, et al., U.S. Pat. No. 4,631,188, for "Injectable Physiologically-Acceptable Polymeric Compositions", issued Dec. 23, 1986
20 Dewitt, "Surgery of the Male Genital Tract", in Family Medicine Principles and Practice, 4th Edition, Taylor, Editor, pp. 778–780 (1994)
21 Park, et al., "New Polymers for Therapeutic Embolization", Poster #47, Meeting of Radiological Society of North America (1993)

All of the above references are herein incorporated by reference in their entirety to the same extent as if each individual reference was specifically and individually indicated to be incorporated herein by reference in its entirety.

2. State of the Art

It is desirable in many clinical situations to embolize blood vessels to prevent/control bleeding (e.g., organ bleeding, gastrointestinal bleeding, vascular bleeding, bleeding associated with an aneurysm) or to ablate diseased tissue (e.g., tumors, etc.). Embolization of blood vessels has heretofore employed certain polymer compositions and particulates, e.g., silicone, metallic coils, sclerosing materials and the like. Because of their ease in delivery, water insoluble non-biodegradable polymers such as cellulose acetate[1,2,3] or ethylene vinyl alcohol[4] dissolved in, for example, DMSO have been employed to embolize blood vessels. These compositions are delivered to the vascular site to be embolized by, for example, a catheter or a syringe. Typically, these compositions will comprise a contrast agent to facilitate guidance of the catheter or syringe to the vascular site as well as the placement of the polymer precipitate which embolizes the blood vessel. Upon contact with the aqueous blood environment at this vascular site, the DMSO dissipates away from the insoluble polymer which results in polymer precipitation and embolization of the blood vessel.

In addition to use in embolizing blood vessels, these compositions can also be employed in the reversible sterilization of mammalian males and females.[5,6]

Vasectomy has been recognized as one of the safest. simplest. and most effective forms of male sterilization.[7,8,20] As normally practiced, this procedure involves a skin incision and some dissection of the vas deferens.[9] Notwithstanding the safety and effectiveness of a vasectomy, such sterilization is difficult to reverse and, at best, only a fraction of vasectomies can be successfully reversed. Accordingly, research has been ongoing to develop new methods of male sterilization for over 30 years.

There are two primary reasons for the continued research into male sterilization. One is that a vasectomy requires a skin incision which is undesirable to most men. The other reason is the lack of certain reversibility.[9]

Several attempts have been made to develop a non-surgical and reversible method of male sterilization.[10,11,12] One such attempt involves the injection of an antifertility agent into the vas deferens of rats and monkeys.[10] The antifertility agent comprises styrene maleic anhydride (SMA) dissolved in dimethylsulfoxide (DMSO). When injected into the vas deferens, the SMA occludes the vas deferens lumen as well as inhibits the fertilizing ability of spermatozoa by virtue of its pH-lowering effect. This sterilization method can be reversed by flushing the SMA out with the solvent DMSO.[10]

Still another attempt involves the injection of a polymeric hydrogel solution in a suitable solvent such as DMSO into the vas deferens.[19] Upon injection into the vas deferens, the polymeric composition slowly coagulates into a spongy polymer structure which takes up water to form a hydrogel composition.

In carrying out such non-surgical procedures, various tests have been employed to verify that the antifertility agent will be or has been injected properly into the vas deferens. One such test is to inject air into a finger-occluded distal section of the vas to see if an air bubble forms.[9] If an air bubble does form, the needle tip is properly placed in the lumen. Another test involves injecting different color dyes into each of the contralateral vas.[9] After the procedure is completed, the subject is asked to urinate. If the color of the urine is a mixture of dyes, then the bilateral injections are successful. However, if the urine color is normal or is one color of the dye or the other, then the procedure is unsuccessful.

It is apparent that such methods for determining whether the antifertility agent is properly injected into the lumen or whether the procedure as a whole is successful have drawbacks. For example, in the air bubble test, if the lumen does not inflate when air is injected, then some skillful maneuvering of the needle tip will be required in order to properly deliver the antifertility agent. With the dye method, success or failure of the procedure cannot be determined until after it has been completed.

In view of the above drawbacks, a need continues to exist in the art for an easy, reliable, and dependable method of sterilizing male mammals.

Still further, the polymeric compositions of this invention do not include compositions which form a hydrogel in situ because, as noted in Stoy.[19] such compositions can cause osmotic shock to neighboring tissue. Furthermore, the coagulation process is rather slow for such hydrogels with only a sponganeous polymer forming in situ. This slow coagulation process could lend itself to migration of at least some of the polymer from the intended site of application prior to formation of the sponganeous polymer. Moreover, at least conceptually, a sponganeous polymer could be open to migration of a small percentage of active sperm through the polymer and into the ejaculate of the male mammal.

SUMMARY OF THE INVENTION

This invention is directed to the discovery of novel polymers which are suitable in compositions useful in in vivo applications such as in embolizing blood vessels and/or reversibly sterilizing mammalian patients. Specifically, this invention is directed to the discovery that unexpected and surprising results are achieved when male mammals are Sterilized with a composition comprising a biocompatible polymer and a biocompatible solvent. In particular, deficiencies associated with each of the prior art procedures are either reduced or eliminated by the invention. Such deficiencies include, for example, problems associated with the proper delivery of the sterilizing agent to the lumen of the vas deferens.

Accordingly, this invention is directed to a method for sterilizing a male mammal, which method comprises delivering a composition comprising a biocompatible polymer and a biocompatible solvent to the vas deferens of the male mammal wherein said delivery is conducted under conditions such that a polymer precipitate forms in situ in the vas deferens thereby sterilizing the male mammal.

In the composition, the biocompatible polymer is preferably an ethylene vinyl alcohol copolymer or a cellulose acetate polymer. The biocompatible solvent is preferably dimethylsulfoxide.

In another embodiment, the biocompatible polymer is replaced with a biocompatible prepolymer. In this embodiment, this invention is directed to a method for sterilizing a male mammal, which method comprises delivering a composition comprising a biocompatible prepolymer to the vas deferens of the male mammal wherein said delivery is conducted under conditions such that said prepolymer polymerizes in situ in the vas deferens thereby sterilizing the male mammal.

In the composition, the prepolymer is preferably selected from the group consisting of cyanoacrylates and urethane prepolymers.

In one optional embodiment, the composition further comprises a biocompatible solvent which is preferably selected from the group consisting of dimethylsulfoxide, ethanol, and acetone.

In another aspect, this invention is directed to a reversible method for sterilizing a male mammal, which method comprises delivering a composition comprising a biocompatible polymer and a first biocompatible solvent to the vas deferens of the male mammal wherein said delivery is conducted under conditions such that a polymer precipitate forms in situ in the vas deferens thereby sterilizing the male mammal and reversing said sterilization by contacting said polymer precipitate formed in the vas deferens with a second biocompatible solvent under conditions such that said polymer precipitate dissolves in said second biocompatible solvent thereby reversing said sterilization of the male mammal.

In one embodiment, the first biocompatible solvent and the second biocompatible solvent are the same.

In the composition, the biocompatible polymer is preferably an ethylene vinyl alcohol copolymer or a cellulose acetate polymer. The first and second biocompatible solvents are preferably dimethylsulfoxide.

DETAILED DESCRIPTION OF THE INVENTION

This invention is directed to methods for sterilizing male mammals, which methods comprise delivering a composition comprising a biocompatible polymer and a biocompatible solvent to the vas deferens of the male mammal.

Prior to discussing this invention in further detail, the following terms will first be defined:

The term "sterilizing" refers to a process for making a person or an animal unable to produce offspring. In the context of this invention, sterilization is carried out by delivering a material into the vas deferens of the male mammal. The material then fills or plugs the lumen of the vas deferens so that spermatic fluid (fluid containing active sperm) ceases to pass therethrough.

The term "biocompatible polymer" refers to polymers which, in the amounts employed, are non-toxic, chemically inert, and substantially non-immunogenic when used internally in the male mammal and which are substantially insoluble in the fluid of the vas deferens. The chemically inert polymers do not appreciably absorb water upon contact with the fluid of the vas deferens and typically will have an equilibrium water content of less than about 25% water and preferably less than about 15% water. Suitable biocompatible polymers include, by way of example, cellulose acetates[13,14,15] (including cellulose diacetate[3]), ethylene vinyl alcohol copolymers[4,16], polyalkyl($C_1$–$C_6$) acrylates, polyalkyl alkacrylates wherein the alkyl and the alk groups contain no more than 6 carbon atoms, polyacrylonitrile and the like. Additional biocompatible polymers are disclosed in U.S. patent application Ser. No. 08/655,822, and entitled "Novel Compositions for Use in Embolizing Blood Vessels" which application is incorporated herein by reference in its entirety. Further examples of biocompatible polymers are provided by Park, et al.[2] Preferably, the biocompatible polymer is also non-inflammatory when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the artisan.

Preferred biocompatible polymers include cellulose diacetate and ethylene vinyl alcohol copolymer. Cellulose diacetate polymers are either commercially available or can be prepared by art-recognized procedures. In a preferred embodiment, the number average molecular weight, as determined by gel permeation chromatography, of the cellulose diacetate composition is from about 25,000 to about 100,000; more preferably from about 50,000 to about 75,000; and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers, Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate, and the like.

Ethylene vinyl alcohol copolymers are either commercially available or can be prepared by art-recognized procedures. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter or needle delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative solubility of the composition in the biocompatible solvent as well as the rate of precipitation of the copolymer in an aqueous solution (e.g., plasma).

The term "biocompatible solvent" refers to an organic material liquid at least at body temperature of the male mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the vas deferens fluid. Preferably, the biocompatible solvent is dimethylsulfoxide.

The term "biocompatible prepolymer" refers to materials which polymerize in situ to form a polymer and which, in the amounts employed, are non-toxic, chemically inert, and substantially non-immunogenic when used internally in the male mammal and which are substantially insoluble in the vas deferens fluid. Suitable biocompatible prepolymers include, by way of example, cyanoacrylates[17,18], urethane prepolymers, and the like. The prepolymer can either be a monomer or a reactive oligomer[17] although reactive oligomers are preferred. Preferably, the biocompatible prepolymer is also non-inflammatory when employed in vivo.

Compositions

The compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of The biocompatible polymer composition based on the total weight of the polymer composition, including biocompatible solvent, and more preferably from about 4 to about 5.2 weight percent. If necessary, gentle heating and stirring can be used to effect dissolution of the biocompatible polymer into the biocompatible solvent, e.g., 12 hours at 50° C.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition may be heat sterilized and then stored preferably in sealed amber bottles or vials until needed.

When the prepolymer is liquid (as in the case of polyurethanes), in the prepolymer compositions the use of a biocompatible solvent is not absolutely necessary but may be preferred to provide for an appropriate viscosity, etc. in the composition. Preferably, when employed, the biocompatible solvent will comprise from about 50 to about 90 weight percent of the biocompatible prepolymer composition based on the total weight of the prepolymer composition and more preferably from about 60 to about 80 weight percent.

In a particularly preferred embodiment, the prepolymer is cyano-acrylate which is preferably employed in the absence of a biocompatible solvent. When so employed, the cyanoacrylate prepolymer is selected to have a viscosity of from about 5 to about 100 centipoise at 20° C.

Methods

The compositions described above can then be employed in methods for sterilizing male mammals. In these methods, the composition is introduced to the vas deferens via conventional catheter or needle technology. See, for example, Chvapil, et al,[8] for a discussion of conventional catheter techniques for introduction of such compositions into the vas deferens. See also, for example, Sheng-cai[9] for a discussion of conventional needle techniques for introduction of such compositions into the vas deferens.

Upon discharge of the composition from the catheter or the needle into the lumen of the vas deferens, the biocompatible solvent dissipates into the vas deferens fluid resulting in the precipitation of the biocompatible polymer. The precipitate forms in the lumen of the vas deferens which acts as a plug to stop the flow of spermatic fluid from the testis.

The particular amount of polymer composition employed is dictated by the diameter of the lumen, the concentration of polymer in the composition, the rate of precipitation (solids formation) of the polymer, etc. Such factors are well within the skill of the artisan. For example, the rate of precipitation can be controlled by changing the overall hydrophobicity/hydrophilicity of the polymer with faster precipitation rates being achieved by a more hydrophobic polymer composition.

One particularly preferred method for delivering the composition to the vas deferens is via a small diameter medical catheter. The particular catheter employed is not critical provided that polymeric catheter components are compatible with the polymeric composition (i.e., the catheter components will not readily degrade in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the composition can be readily determined by the skilled artisan and include, for example, other polyolefins. fluoropolymers (e.g., Teflon®), silicone, etc.

When delivered by catheter, the injection rate of the polymer composition dictates, in part, the form of the precipitate in the lumen of the vas deferens. Specifically, low injection rates of approximately 0.05 to 0.3 cc/minute will provide for a precipitate in the form of a kernel or nodule which is particularly beneficial because the precipitate forms primarily at the point of injection.

When introduced into the lumen of the vas deferens, the biocompatible solvent rapidly diffuses into the fluid present in the vas deferens leaving a solid precipitate in the lumen. Without being limited to any theory, it is believed that initially, a soft gel to spongy solid precipitate forms upon contact with the vas deferens fluid. This precipitate then restricts semen flow from the testis thereby sterilizing the male mammal.

The methods described herein can also employ a biocompatible prepolymer such as a urethane or cyanoacrylate prepolymer in place of or in conjunction with the polymer composition described above. When the prepolymer is liquid (as in the case of cyanoacrylates), the use of a biocompatible solvent is not absolutely necessary but may be preferred to provide for an appropriate viscosity, etc. in the composition. Upon injection into the vas deferens, the prepolymer will polymerize in situ upon contact with the vas deferens fluid and form a solid polymer in the lumen of the vas deferens. The solid polymer blocks the passage of spermatic fluid from the testis of the male mammal thereby sterilizing the male mammal.

Without being limited to any theory, the methods of this invention address prior art problems because the above-described sterilization procedure can be easily and reliably reversed. In such a case, the same procedures as sterilization are carried out except without the use of a biocompatible polymer. Specifically, a composition comprising a biocompatible solvent is delivered to the vas deferens at or near the location of the polymer precipitate previously deposited therein. The biocompatible solvent acts to dissolve and flush out the polymer precipitate. The lumen of the vas deferens is thereby restored to its previous condition and spermatic fluid can again pass therethrough.

Utility

The methods described herein are useful in sterilizing male mammals which, in turn, can be used to prevent/control reproduction. Accordingly, these methods find use in human and other mammalian subjects requiring sterilization.

EXAMPLES

Unless otherwise stated, all temperatures are in degrees Celsius. Also, in these examples, unless otherwise defined below, the abbreviations employed have their generally accepted meaning:

cc=cubic centimeter cps=centipoise

DMSO=dimethylsulfoxide gm=gram mL=milliliter

RT=room temperature

EVOH=ethylene vinyl alcohol copolymer mm=millimeter $\mu$m=micron

In the following examples. Examples 1–2 illustrate the preparation of polymer compositions useful in the methods described herein which polymer compositions comprise cellulose acetate and EVOH. Examples 3 and 4 illustrate how such polymer compositions could. be used in the methods of this invention.

Examples 1

A cellulose diacetate polymer composition was prepared by dissolving cellulose acetate (39.7 weight percent acetyl content) into DMSO to provide for an 6.8 weight percent concentration of the polymer in DMSO.

Example 2

An EVOH polymer composition was prepared by dissolving EVOH (44 mole percent ethylene) into DMSO to provide for an 6.8 weight percent concentration of the copolymer in DMSO. In order to facilitate dissolution, the system can be heated to 50° C. overnight.

Example 3

The purpose of this example is to illustrate how an in vivo application of the methods of this invention in the sterilization of a male mammal could be accomplished.

In this example, a 50 pound male dog is prepared for sterilization using a composition comprising 5.8 weight percent EVOH polymer (containing 48 weight percent ethylene), in DMSO. This composition is loaded into a syringe having a needle attached thereto. Local procaine anaesthesia is applied to the scrotum area of the subject. The vas deferens of one side is gripped through the skin by a vas-fixation clamp and lifted. The syringe needle is used to puncture the vas in the direction away from the testis. The EVOH polymer composition (0.3 cc) is then delivered to the lumen of the vas deferens. After delivery, the DMSO in the EVOH composition rapidly diffuses and the EVOH precipitates in the lumen resulting in a blockage of the vas deferens. After about 5 minutes, the polymer is fully precipitated and the syringe needle is removed from vas.

The same procedure is repeated with the other vas deferens of the male subject.

Example 4

The purpose of this example is to illustrate how an in vivo application of the methods of this invention in reversing the sterilization of a male mammal could be accomplished.

In this example, the procedures of Example 3 are followed except that the polymer composition is replaced with only the biocompatible solvent. Approximately 0.3 to 0.5 cc of DMSO is injected int6 the occluded vas deferens over a period of 1 to 2 minutes to dissolve the previously deposited polymer precipitate which is removed by pulling back on the syringe. The procedure is repeated twice more. After about 10 minutes, the polymer is fully dissolved and evacuated, and the syringe needle is removed from the vas.

Example 5

The purpose of this example is to illustrate ex vivo reversibility of the process. Specifically, six (6) segments of coronary arteries were excised from fresh lamb hearts, obtained from a local meat store that day. The arteries (vessels) were approximately 6 cm in length and varied in diameter from about 1.5 to about 3.0 mm. Each segment was washed and then flushed with normal saline at room temperature.

The vessel segments were placed in a beaker filled with normal saline and a polymer composition comprising 7 weight percent cellulose acetate polymer (39% acetyl content) in DMSO was injected from a 3 cc syringe into each vessel through a 20 gage needle. Approximately 1 to 3 cm of each vessel was filled with the polymer composition and injection was over a 10 to 15 second period. Attempts to flush the vessel with normal saline showed no flow or total vessel occlusion.

After 15 minutes, a new 3 cc syringe and 20 gage needle filled with DMSO was introduced into the vessel, just proximal to the polymer plug. Gentle injection/aspiration of the DMSO over a 1 minute period yielded a noticeable dissolution of the polymer, with recanalization of the vessel within 2 to 3 minutes. Dissolution of the polymer plug took about 5 minutes. This result was repeated in all vessel segment samples.

Based on the above, this procedure is preferably conducted using a catheter flush/aspiration system to capture all of the solvent and polymer.

It is understood that the same procedures set forth above can be employed with compositions employing liquid prepolymers. However, when so employed, the timing and injection rates will vary depending on the cure rate for the prepolymer. Such factors are within the skill of the artisan.

From the foregoing description, various modifications and changes in the composition and method will occur to those skilled in the art. All such modifications coming within the scope of the appended claims are intended to be included therein.

What is claimed is:

1. A method of sterilizing a male mammal, wherein said sterilization is reversible, which method comprises delivering a composition comprising:
   (a) a chemically-inert biocompatible polymer having an equilibrium water content of less than about 15%, and
   (b) a biocompatible solvent,
   wherein said composition is delivered under conditions such that a polymer precipitate forms in situ in the vas deferens of said male mammal, thereby sterilizing said male mammal.

2. The method according to claim 1, wherein said biocompatible polymer is selected from the group consisting of cellulose acetate polymers, ethylene vinyl alcohol copolymers, and polyacrylates.

3. The method according to claim 2, wherein said biocompatible polymer is a cellulose acetate polymer or an ethylene vinyl alcohol copolymer.

4. The method according to claim 1, wherein said biocompatible solvent is selected from the group consisting of dimethylsulfoxide, ethanol, and acetone.

5. The method according to claim 4, wherein said biocompatible solvent is dimethylsulfoxide.

6. The method according to claim 1, wherein said composition is delivered to said vas deferens via a catheter.

7. The method according to claim 1, wherein said composition is delivered to said vas deferens via a needle.

8. A reversible method for sterilizing a male mammal, which method comprises delivering a composition comprising:
   (a) a chemically-inert biocompatible polymer having an equilibrium water content of less than about 15%, and
   (b) a first biocompatible solvent to the vas deferens of said male mammal,
   wherein said composition is delivered under conditions such that a polymer precipitate forms in situ in said vas deferens of said male mammal, thereby sterilizing said male mammal, and further wherein said sterilization is reversed by contacting said polymer precipitate formed in said vas deferens of said male mammal with a second biocompatible solvent, thereby reversing sterilization of said male mammal.

9. The method according to claim 8, wherein said biocompatible polymer is selected from the group consisting of cellulose acetate polymers, ethylene vinyl copolymers, and polyacrylates.

10. The method according to claim 9, wherein said biocompatible polymer is a cellulose acetate polymer or an ethylene vinyl alcohol copolymer.

11. The method according to claim 8, wherein said first biocompatible solvent and said second biocompatible solvent are the same solvent.

12. The method according to claim 8, wherein each of said first biocompatible solvent and said second biocompatible solvent is selected from the group consisting of dimethylsulfoxide, ethanol, and acetone.

13. The method according to claim 12, wherein said first biocompatible solvent and said second biocompatible solvent are dimethylsulfoxide.

14. The method according to claim 8, wherein said composition is delivered to said vas deferens via a catheter or a needle.

15. The method according to claim 8, wherein said second biocompatible solvent is delivered to said vas deferens via a catheter or a needle.

16. The method according to claim 8, wherein said second biocompatible solvent is dimethylsulfoxide.

* * * * *